United States Patent

Tano et al.

[11] Patent Number: 5,562,691
[45] Date of Patent: Oct. 8, 1996

[54] OPHTHALMIC SURGICAL APPARATUS

[75] Inventors: Yasuo Tano, Kobe; Kiyoshi Makihara, Gamagori, both of Japan

[73] Assignee: Nidek Co., Ltd., Japan

[21] Appl. No.: 267,364

[22] Filed: Jun. 29, 1994

[30] Foreign Application Priority Data

Sep. 30, 1993 [JP] Japan .................................. 5-269962

[51] Int. Cl.$^6$ ................................................ A61B 17/32
[52] U.S. Cl. ............................................. 606/166; 604/22
[58] Field of Search .................................. 606/108, 166, 606/167, 170, 171; 604/22

[56] References Cited

U.S. PATENT DOCUMENTS

| | | | |
|---|---|---|---|
| 4,570,632 | 2/1986 | Woods | 606/166 |
| 4,577,629 | 3/1986 | Martinez | 604/22 |
| 4,753,234 | 6/1988 | Martinez | 604/22 |
| 5,226,910 | 7/1993 | Kajiyama et al. | 604/22 |
| 5,275,607 | 1/1994 | Lo et al. | 604/22 |

OTHER PUBLICATIONS

Escalon, Fall 1992 Catalog by Escalon Trek Medical Precision Instruments for Brilliant Intraocular Surgery by Optikon.

*Primary Examiner*—Michael Powell Buiz
*Assistant Examiner*—W. Lewis
*Attorney, Agent, or Firm*—Rossi & Associates

[57] ABSTRACT

An ophthalmic surgical apparatus for vitreous surgery in the eyeball comprises a probe provided with a guide knife, having an end portion formed in a predetermined curve, and a dissecting knife movable along the curve of the guide knife to dissect proliferated membrane, moving device that moves the dissecting knife so as to reciprocate between an initial position and the end portion of the guide knife.

18 Claims, 4 Drawing Sheets

OPHTHALMIC SURGICAL APPARATUS

BACKGROUND OF THE INVENTION

1. Field of the Invention

The present invention relates to ophthalmic surgical apparatus for vitreous surgery, and more particularly to apparatus for dissecting proliferative membrane of the retinal surface or adjacent ocular tissue.

2. Description of Related Art

Vitreous surgery is carried out to remove opacities out of the vitreous body thereby to reconstruct an optical path therein, and to excise proliferative tissue of the retinal surface which may cause retinal detachment so that retinal reattachment is achieved. Simple opacity excision can be performed relatively easily through the recent improvement of vitreous surgical apparatuses, instruments and techniques. Dissecting proliferative membrane from the retina, however, is considered as a surgery requiring the most difficult and highest skill in vitreous surgeries, because it needs delicate maneuvers within an extremely limited space inside an eyeball.

In a conventional basic operation to dissect proliferated membrane of the retinal surface, a hook, a pick and the like is inserted into an eyeball to hook a part of the proliferated membrane thereon and to remove the proliferated membrane off the retina while slowly raising it. In a case of strong adhesion of proliferated membrane to the retina, intraocular scissors may be used to cut the adhesion of the proliferated membrane.

Such a pick, a hook and the like requiring very fine handling, there were cases where an inexperienced surgeon stuck a pick too deep in the eyeball or hooked non-proliferated portions too much with the pick, and the retina of a patient was injured by mistake consequently.

And also, the surgery with pick resulted in cutting proliferated membrane off, could not raise it well. Surgeon therefore had to start over again hooking the proliferated membrane. When the proliferated membrane could not be dissected with only a pick according to situations of adhesion of the proliferated membrane, the surgeon had to exchange the pick for intraocular scissors and to insert it again into the eyeball. Consequently, there were some cases where the surgery took a very long time.

SUMMARY OF THE INVENTION

The present invention has been made in view of the above circumstances and has an object to overcome the above problems and to provide an ophthalmic surgical apparatus capable of performing dissection of proliferated membrane of the retinal surface safely and effectively irrespective of surgeon's skill.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic surgical apparatus, for operating vitreous body of eyeball, of this invention comprises a probe provided with a guide knife, an end portion of which is formed in a predetermined curve, and a dissecting knife movable along the curve of the guide knife, for dissecting proliferated membrane, and moving means for moving the dissecting knife so as to reciprocate between an initial position and the end portion of the guide knife.

More specifically, an ophthalmic surgical apparatus of this invention comprises a grip member to be held by surgeon in his hand, a guide knife an end portion of which is formed in a predetermined curve, fixed to the grip member, a dissecting knife of elasticity movable along the curve of the guide knife, the end portion of which is formed wider that that of the guide knife, a piston movable in an air chamber inside the grip member, a tube for connecting the air chamber and a compressed air source, a solenoid valve disposed in a flow path of compressed air into the air chamber, to make the compressed air flow into the air chamber and discharge out of same, control means for controlling switching operation of the solenoid valve, and a foot switch connected to the control means, to transmit a signal to switch the solenoid valve.

According to the present invention, dissection of proliferated membrane of the retinal surface can be carried out safely and effectively without requiring high skill and experience.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of a preferred embodiment of ophthalmic surgical apparatus embodying the present invention will now be given referring to the accompanying drawings.

Figure 1:
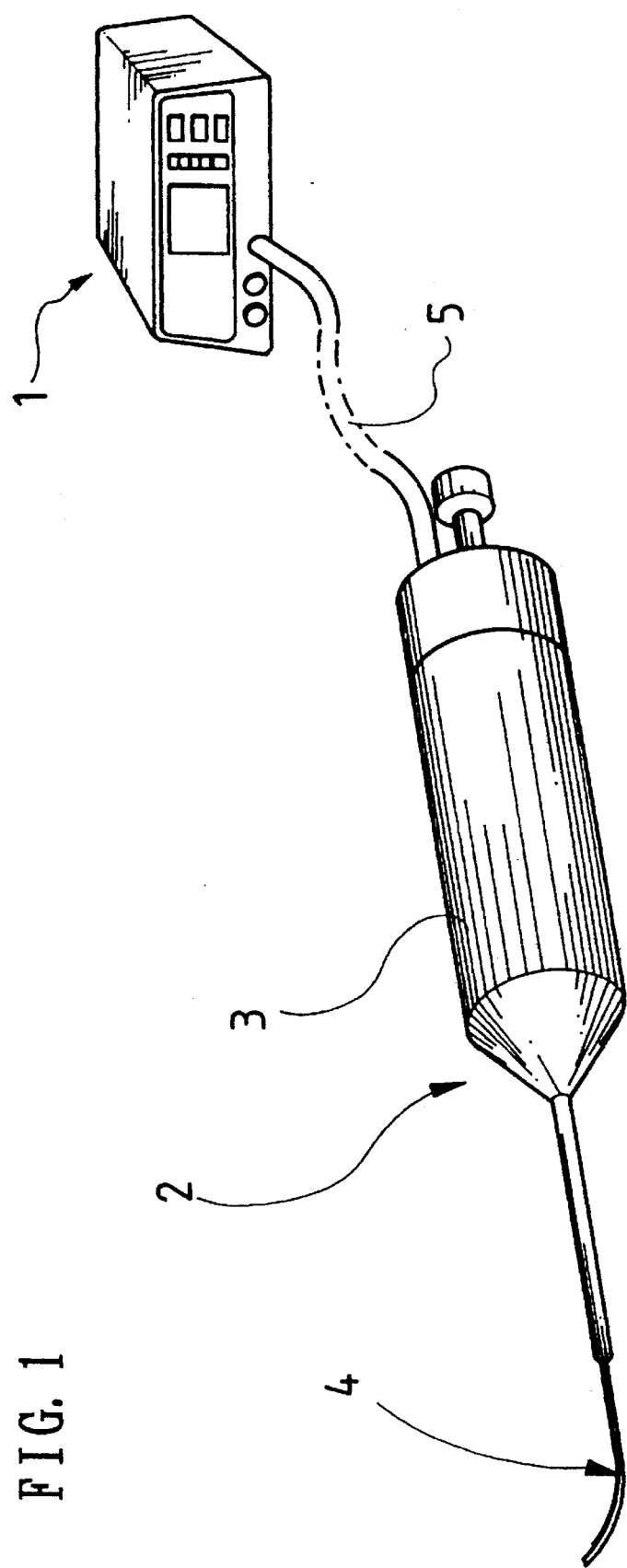
FIG. 1 is an exterior perspective view of a vitreous surgical apparatus in an embodiment according to the present invention.

FIG. 1 shows a surgical apparatus for vitreous body in an embodiment. The surgical apparatus comprises an apparatus unit 1 and a probe member 2 for dissecting proliferated membrane, which is connected to the apparatus unit 1. The probe 2 is constructed of a grip member 3, a dissecting knife member 4 and an air tube 5.

Figure 2:
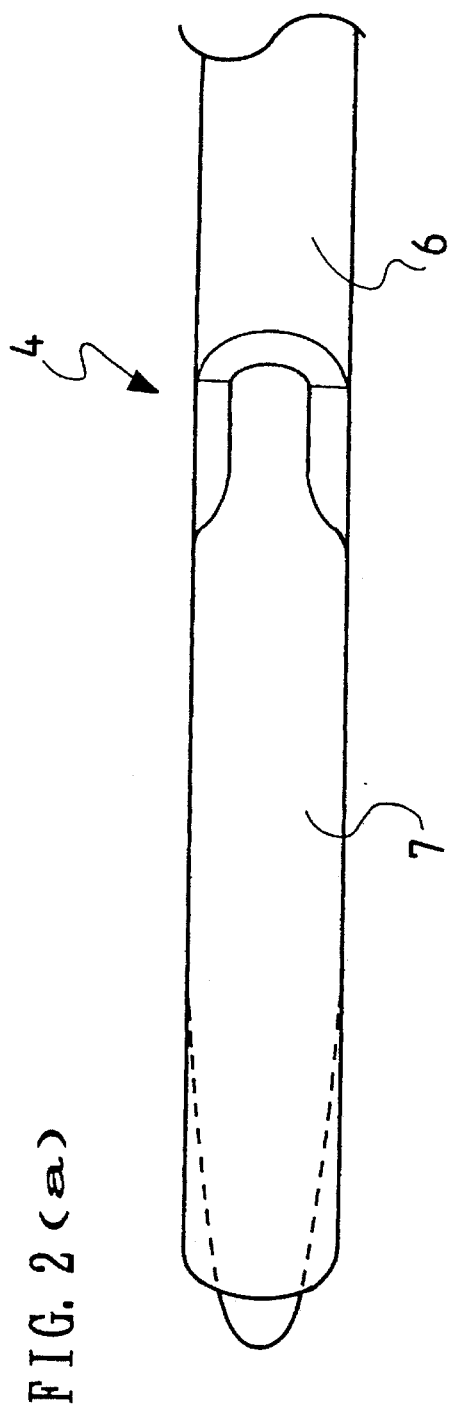
FIG. 2(a) is a plan view of showing a dissecting knife member 4 in an embodiment according to the present invention.
FIG. 2(b) is a longitudinal sectional view of the dissecting knife member 4 in an embodiment according to the present invention.
Figure 2:
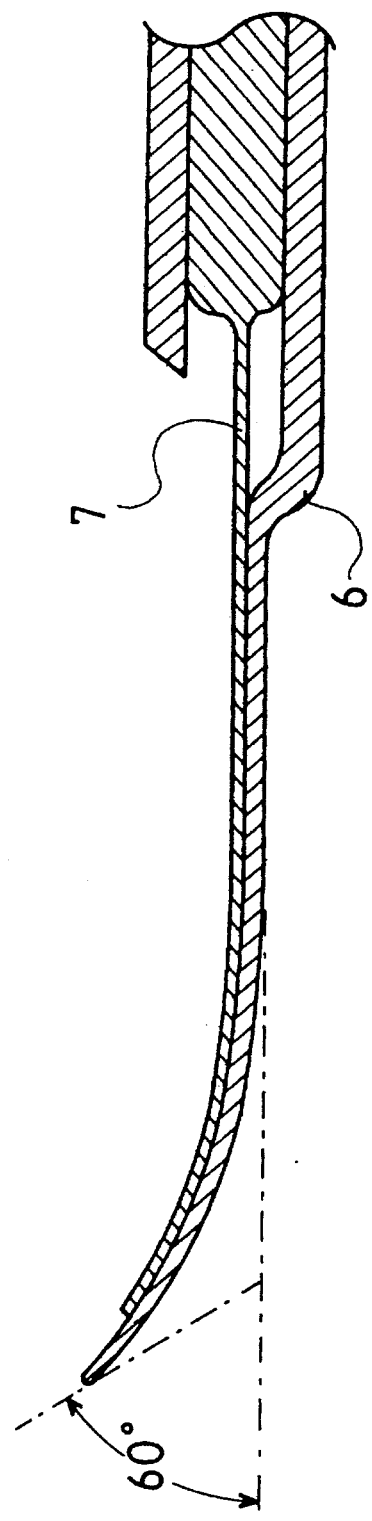
Figure 3:
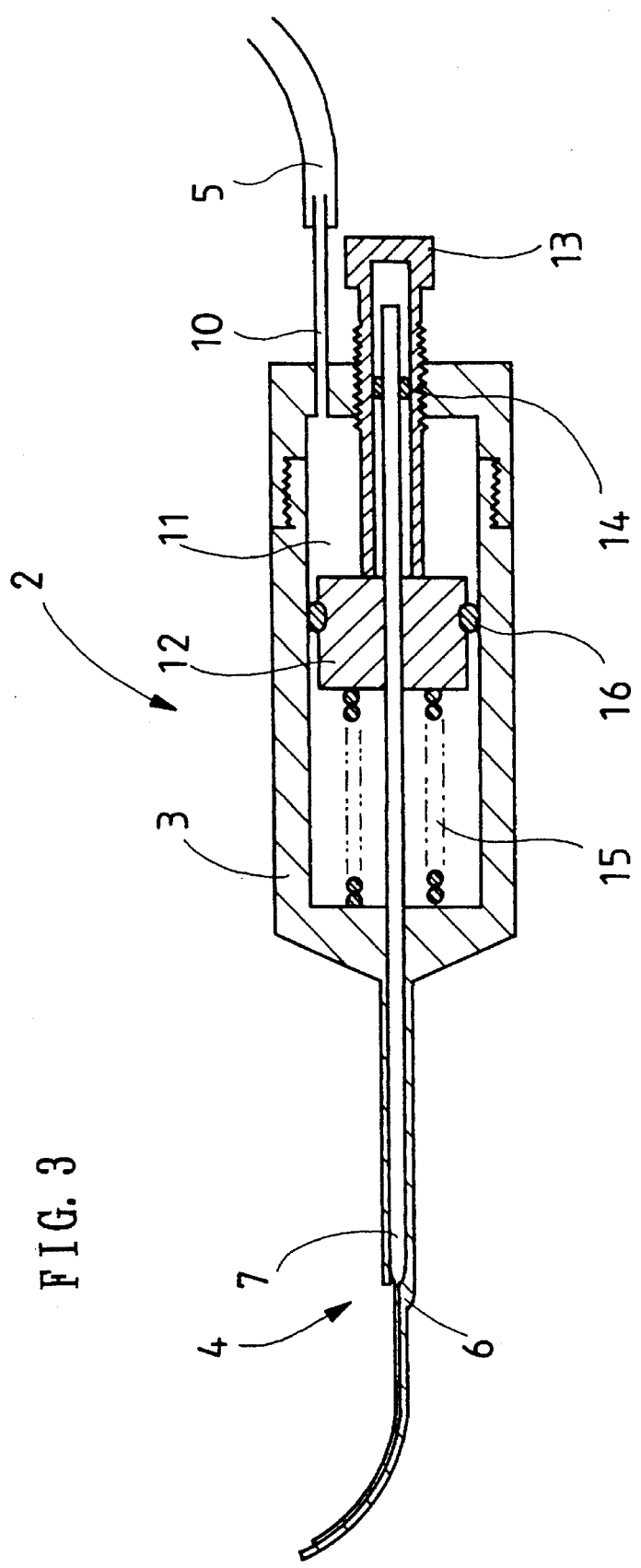
FIG. 3 is a longitudinal sectional schematic view of a grip member 3 of a probe 2 in an embodiment according to the present invention.

The probe member 2 is shown in detail in FIGS. 2(a), 2(b) and 3.

FIG. 2(a) shows a plan view of the dissecting knife member 4 of the probe 2 and FIG. 2(b) shows a longitudinal sectional view of same.

The dissecting knife member 4 is constituted of a fixed knife 6 and a movable knife 7. The fixed knife 6 has a pipe shape in one end from the central portion thereof (right side in the figure), the end portion of which is connected with the grip member 3, and a tapered plate shape in the other end (left side in the figure), the tapered end portion of which is curved upward. The curve is designed so that a tangent to a top point of the curve is at an angle of 60° with a longitudinal axis of the grip member 3 as shown in FIG. 2(b), and further so as to about correspond with a curved surface of the fundus of a standard eye when the detaching knife member 4 is inserted in the eye for proliferated membrane dissecting surgeries. The curve of the fixed knife 6 may be varied according to operability in surgery, structure and others of the dissecting knife member 4.

The movable knife 7 is constituted of a rod portion inserted in the pipe portion of the fixed knife 6 and a plate portion elongated from the rod portion. The plate portion of the movable knife 7 is made of elastic materials, so that the plate portion moves along the curved surface of the fixed knife 8 when the rod portion moves forward and backward (right and left in the figure) in the pipe portion of the fixed knife 6. And the end of the plate portion of the movable knife 7 is formed so as to be wider than that of the fixed knife 6. The movable knife 7 accordingly moves to almost an end position of the fixed knife 6.

In the embodiment, the fixed knife and the dissecting knife are both made of stainless steel, and the plate portion of the dissecting knife is formed thinner than that of the fixed knife so that it has elasticity. For materials of the both knives, it is also possible to use synthetic resin and others.

FIG. 3 shows a schematic longitudinal sectional view of the probe 2.

The grip member 3 is provided with an air pipe 10 connected with the air tube 5, a piston 12, an adjusting screw 13 to adjust an initial position of the piston 12 and a spring 15. Compressed air is delivered into an air chamber 11 inside the grip member 3 through the air pipe 10 from the air tube 5, and presses the piston 12 to move. The movable knife 7, being fixed in the piston 12 at the rod portion, moves as the piston 12 pressed by compressed air moves. The adjusting screw 13 supports the movable knife 7 through an O-ring 14 so that the movable knife 7 moves in the axis direction. The position of the adjusting screw 13 is not limited to an axial center of the probe 2 and may be at a periphery of the axial center.

The spring 15 presses the piston 12 toward the adjusting screw 13, the piston 12 moves, accordingly, toward the adjusting screw 13 as the compressed air in the air chamber 11 is reduced. O-ring 16 disposed at the periphery of the piston 12 retains airtightness of the air chamber 11.

For moving the movable knife 7, some methods with a combination of electric motor and cam, with electromagnet may also be utilized, without limiting the above way.

Surgery of the above constructed apparatus will be explained as below, referring to a block diagram of a control system shown in FIG. 4.

Surgeon, first, inserts the dissecting knife member 4 in an eyeball of a patient with the grip member 3 of the probe 2 in his hand and hooks a part of proliferated membrane of the retinal surface with a top end portion of the fixed knife 6 and puts the fixed knife 6 therein.

Figure 4:
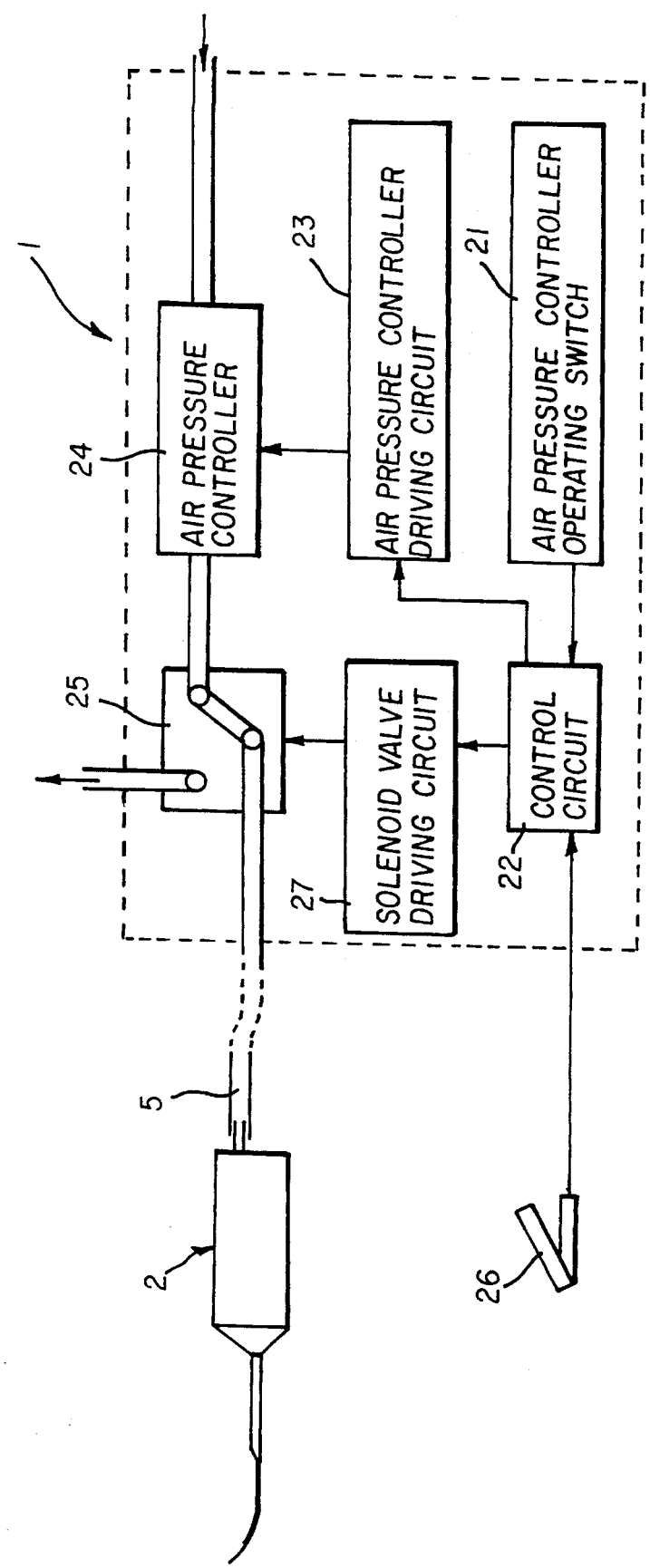
FIG. 4 is a block diagram of a control system according to the present invention.

As shown in FIG. 4, a control system of the apparatus unit 1 contains an air pressure controller operating switch 21 to select a compressing pressure of air, a control circuit 22, an air pressure controller driving circuit 23, an air pressure controller 24, a solenoid valve 25 provided with an inlet port disposed in the air pressure controller 24 side and an outlet port and a solenoid valve driving circuit 27. A signal input at the air pressure controller operating switch 21 is transmitted to the control circuit 22. The control circuit 22 then drives the air pressure controller 24 via the air pressure controller driving circuit 23, so that compressed air of designated pressure is produced.

Delivery of compressed air to the probe 2 and exhaust of same out of the probe 2 alternately are carried out through the solenoid valve 25. Specifically, when an inlet port of the valve 25 is connected with the air tube 5, compressed air flows into the air chamber 11 and moves the piston 12 against pressure of the spring 15. When an outlet port of the valve 25 is connected with the air tube 5, alternatively, compressed air within the air chamber 11 flows out of same and the piston 12 is returned to its former position by the pressure of the spring 15 accordingly.

In the above constructed apparatus, when a foot switch 26 connected to the apparatus unit 1 is worked by the surgeon, then a signal thereof is input to the control circuit 22. The control circuit 22 drives the solenoid valve 25 through the solenoid valve control circuit 27, so that delivery of compressed air to the probe 2 and exhaust of same out of the probe 2 are repeated alternately at predetermined intervals.

As the piston 12 reciprocates as explained above, the top end portion of the movable knife 7 fixedly supported in the piston 12 reciprocates between the initial position and almost the end of the fixed knife 6 while being guided with the fixed knife 6. The wide end portion of the movable knife 7 intermittently reciprocating dissects the proliferated membrane accordingly.

The present invention may be embodied in other specific forms without departing from the spirit or essential characteristics thereof. The above embodiment shows an embodiment of repeating intermittent reciprocating motion of the movable knife 7 with the solenoid valve 25, while it is possible to supplement a function, for instance, that detects operating amount of the foot switch and changes pressure of compressed air to be delivered in an air chamber according to the operating amount to adjust moving amount of a movable knife. Instead of intermittent reciprocating motion of the movable knife, it is further possible to manually carry out reciprocating motion of the movable knife 7 by combining a position of the foot switch operated with a position of the movable knife 7. In case of fine controlling as above, driving way by motor also used for moving the movable knife 7.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic surgical apparatus for vitreous surgery in the eyeball, comprising:

a probe provided with a guide knife, said guide knife being substantially planar and having an end portion which is formed in a predetermined curve, and a dissecting knife, said dissecting knife being substantially planar and movable along the curve of the guide knife, for dissecting proliferated membrane;

moving means for moving said dissecting knife so as to reciprocate between an initial position and the end portion of the guide knife.

2. The ophthalmic surgical apparatus according to claim 1, wherein the dissecting knife is made of elastic member, elasticity of which enables the dissecting knife to move along the curved end of the guide knife at the time of reciprocation.

3. The ophthalmic surgical apparatus according to claim 1, wherein the guide knife is curved about corresponding to a surface of the eye fundus.

4. The ophthalmic surgical apparatus according to claim 1, wherein the moving means comprises a piston fixed to the dissecting knife and movable in an air chamber provided inside the probe, a tube through which compressed air flows from an air source into the air chamber and discharges out of same, a solenoid valve to carry out a flow of compressed air into the air chamber and a discharge of same out of the air chamber, and control means for controlling switching of the solenoid valve.

5. The ophthalmic surgical apparatus according to claim 1, further comprising changing means for changing an initial position of the dissecting knife.

6. The ophthalmic surgical apparatus according to claim 1, wherein both the guide knife and the dissecting knife have cutting edges for dissection.

7. The ophthalmic surgical apparatus according to claim 1, wherein said dissecting knife reciprocates between an initial position and an end position, said end position being at the end portion of said guide knife, but not beyond said end portion.

8. An ophthalmic surgical apparatus for vitreous surgery in the eyeball, comprising:

a probe provided with a guide knife, an end portion of which is formed in a predetermined curve, and a dissecting knife movable along the curve of the guide knife, for dissecting proliferated membrane;

moving means for moving said dissecting knife so as to reciprocate between an initial position and the end portion of the guide knife; and wherein the end portion of the guide knife is formed in a tapered shape so as to hook a part of the proliferated membrane and the end portion of the dissecting knife is formed in a wider shape than that of the guide knife.

9. An ophthalmic surgical apparatus for dissecting proliferated membrane in vitreous body, comprising:

a probe provided with a grip member to be held by surgeon in his hand, a guide knife fixed to the grip member, said guide knife being substantially planar and having a predetermined curved end portion, and a dissecting knife, said dissecting knife being substantially planar and movable along the curved end of the guide knife for dissecting proliferated membrane;

driving means for reciprocating the dissecting knife between an initial position and the end portion of the guide knife;

control means for controlling reciprocation of the dissecting knife, and a switch connected to the control means for transmitting a signal to order the motion of the dissecting knife, connected to the control means.

10. The ophthalmic surgical apparatus according to claim 9, wherein the dissecting knife is made of elastic member, elasticity of which enables the dissecting knife to move along the curved end of the guide knife at the time of reciprocation.

11. The ophthalmic surgical apparatus according to claim 9, wherein the guide knife is curved about corresponding to a surface of the eye fundus.

12. The ophthalmic surgical apparatus according to claim 9, further comprising changing means for changing an initial position of the dissecting knife.

13. The ophthalmic surgical apparatus according to claim 9, wherein the control means controls the reciprocation of the dissecting knife so as to be performed in a predetermined cycle.

14. The ophthalmic surgical apparatus according to claim 9, wherein both the guide knife and the dissecting knife have cutting edges for dissection.

15. The ophthalmic surgical apparatus according to claim 9, wherein said dissecting knife reciprocates between an initial position and an end position, said end position being at the end portion of said guide knife, but not beyond said end portion.

16. An ophthalmic surgical apparatus for dissecting proliferated membrane in vitreous body, comprising:

a probe provided with a grip member to be held by surgeon in his hand, a guide knife fixed to the grip member, having a predetermined curved end portion, and a dissecting knife movable along the curved end of the guide knife for dissecting proliferated membrane;

driving means for reciprocating the dissecting knife between an initial position and the end portion of the guide knife;

control means for controlling reciprocation of the dissecting knife;

a switch connected to the control means for transmitting a signal to order the motion of the dissecting knife; and wherein the end portion of the guide knife is formed in a tapered shape so as to hook a part of the proliferated membrane and the end portion of the dissecting knife is formed in a wider shape than that of the guide knife.

17. An ophthalmic surgical apparatus for dissecting proliferated membrane of vitreous body, comprising:

a grip member to be held by a surgeon in his hand;

a guide knife, being substantially planar and having an end portion which is formed in a predetermined curve, fixed to the grip member;

a dissecting knife being substantially planar and being elastically movable along the curve of the guide knife;

a piston movable in an air chamber inside the grip member;

a tube for connecting the air chamber and a compressed air source;

a solenoid valve disposed in a flow path of compressed air into the air chamber, to make the compressed air flow into the air chamber and discharge our of same;

control means for controlling switching operation of the solenoid valve; and a foot switch connected to the control means, to transmit a signal to switch the solenoid valve.

18. The ophthalmic surgical apparatus according to claim 17, wherein both the guide knife and the dissecting knife have cutting edges for dissection.

* * * * *